(12) United States Patent
Framroze

(10) Patent No.: US 9,440,932 B2
(45) Date of Patent: Sep. 13, 2016

(54) PHASE-TRANSFER CATALYSED FORMATION OF N-(SUBSTITUTED PHENYL) SULFONAMIDES IN WATER

(71) Applicant: Bomi P Framroze, Mumbai (IN)

(72) Inventor: Bomi P Framroze, Mumbai (IN)

( * ) Notice: Subject to any disclaimer, the term of this patent is extended or adjusted under 35 U.S.C. 154(b) by 0 days.

(21) Appl. No.: 14/338,357

(22) Filed: Jul. 23, 2014

(65) Prior Publication Data

US 2016/0024028 A1    Jan. 28, 2016

(51) Int. Cl.
*C07D 249/12*    (2006.01)

(52) U.S. Cl.
CPC ............ *C07D 249/12* (2013.01); *Y02P 20/582* (2015.11)

(58) Field of Classification Search
CPC .................................................. C07D 249/12
See application file for complete search history.

(56) References Cited

U.S. PATENT DOCUMENTS

2003/0236437 A1* 12/2003 Smeltz .................. C07C 303/38
564/395

OTHER PUBLICATIONS

Freedman, 1986, Pure & Appl. Chem. vol. 58, No. 6, p. 857-868.*

* cited by examiner

*Primary Examiner* — Michael Barker
*Assistant Examiner* — Karen Cheng
(74) *Attorney, Agent, or Firm* — Altimatia, LLC; David M. Gange

(57) ABSTRACT

A new process for making agrochemically important N-[2,4-dichloro-5-[4-(difluoro methyl)-4,5-dihydro-3-methyl-5-oxo-1H-1,2,4-triazol-1-yl] phenyl]methanesulfonamide by reacting 1-(5-amino-2,4-dichlorophenyl)-4,5-dihydro-4-difluoromethyl-3-methyl-1,2,4-triazol-5(1H)-one and methanesulfonyl chloride in water using an inorganic base to dynamically control the reaction pH and in the presence of a phase transfer catalyst suspended in an 1:1 aromatic solution.

8 Claims, No Drawings

PHASE-TRANSFER CATALYSED FORMATION OF N-(SUBSTITUTED PHENYL) SULFONAMIDES IN WATER

FIELD

This invention relates to a new process for making agrochemically important N-[2,4-dichloro-5-[4-(difluoromethyl)-4,5-dihydro-3-methyl-5-oxo-1H-1,2,4-triazol-1-yl]phenyl]methanesulfonamide by reacting 1-(5-amino-2,4-dichlorophenyl)-4,5-dihydro-4-difluoromethyl-3-methyl-1,2,4-triazol-5(1H)-one and methanesulfonyl chloride in water using an inorganic base to dynamically control the reaction pH and in the presence of a phase transfer catalyst suspended in an 1:1 aromatic solution. The described process is environmentally benign being carried out in water instead of organic solvents, does not require the use of any organic base and reagent recycle steps. Further the process of this invention results in high purity of the desired mono sulfonamide product eliminating the need to remove the typically formed bis-sulfonamide impurity.

BACKGROUND

N-[2,4-dichloro-5-[4-(difluoromethyl)-4,5-dihydro-3-methyl-5-oxo-1H-1,2,4-triazol-1-yl]phenyl]methanesulfonamide is an important herbicide in the agrochemical industry. The ability for general, efficient syntheses of sulfonamides under mild conditions is still of continuing interest to the industry. Recently many efforts have been made for the development of novel processes to make sulfonamides such as described in (a) S. W. Wright and K. N. Hallstrorn, *J. Org. Chem.*, 2006, 71, 1080-1084; (b) A. R. Katritzky, A. A. A. Abdel-Fattah, A. V. Vakulenko and H. Tao, *J. Org. Chem.*, 2005, 70, 9191-9197; (c) S. Caddick, J. D. Wilden and D. B. Judd, *J. Am. Chem. Soc.*, 2004, 126, 1024-1025; (d) R. Pandya, T. Murashima. L. Tedesehi and A. G. M. Barrett, *J. Org. Chem* 2003, 68, 8274-2876; (e) J. W. Lee, Y. Q. Louie, D. P. Walsh and Y.-T. Chang, *J. Comb. Chem.*, 2003, 5, 330-335; (f) C. G. Frost, J. P. Hartley and D. Griffin, *Synlett*, 2002, 11, 1928-1930.

However, the conventional synthesis for reaction of an amino compound and a sulfonyl chlorides is still the best method because of the simplicity of the reaction. Two general schemes for this reaction are widely used and described in the prior art. The first is to perform the reaction in organic solvents and employ organic amine bases to scavenge the acid that is generated for example as described in U.S. Pat. No. 4,818,275. Elevated temperature is often required, especially for the less reactive aniline substrates and bis-sulfonylation is a common side reaction, which makes isolation difficult and expensive and adds the further recycle of the stoichiometric quantity of acid scavenger used such as pyridine or triethyl amine as an unnecessary processing step. Modifications of this basic method can also be seen in the prior art for example with the use of catalytic quantity of acid scavengers and higher temperature boiling solvents such as described in U.S. Pat. No. 7,169,952.

The second general scheme uses modified Schotten-Baumann conditions. Here a typical procedure involves adding the sulfonyl chloride slowly into an amine solution in a biphasic system of organic solvents and basic (sodium carbonate or sodium hydroxide) aqueous solution such as described in (a) M. D. Surman, M. J. Mulvihill and M. J. Miller, *Org. Lett.*, 2002, 4, 139-141; (b) W. Hu, Z. Guo, F. Chu, A. Bai, X. Yi, G. Cheng and J. Li, *Bioorg. Med. Chem.*, 2003, 11, 1153-1160; (c) M. Medebielle, O. Onomura, R. Keirouz, E. Okada, H. Yano and T. Terauchi, *Synthesis*, 2002, 17, 2601-2608; (d) C. Goldenberg, R. Wandestrick and J. Richard, *Eur. J. Med. Chem*, 1977, 12, 81-86. Water as a reaction solvent is preferred over organic solvents due to cost, safety and environmental concerns.

Under these conditions, hydrolysis of the sulfonyl chlorides is the major competing reaction, which necessitates the use of excess sulfonyl chloride and results in diminishing yields. In both processes, the isolation and purification of the sulfonamide products are not straightforward due to the formation of bis-sulfonated impurities and large quantities of hydrolysed sulfonic acid by-products formed.

Accordingly, there exists a need to prepare N-(substituted aryl)sulfonamides directly from arylamines in an environmentally benign manner without the addition of an acid scavenger and without substantial formation of the bis (methanesulfonylamino) and hydrolyzed sulfonyl chloride by-products.

SUMMARY OF THE INVENTION

The present invention describes a modified Schitten-Baumann process that is facile, and environmentally benign for preparing N-[2,4-dichloro-5-[4-(difluoromethyl)-4,5-dihydro-3-methyl-5-oxo-1H-1,2,4-triazol-1-yl]phenyl]methanesulfonamide by reacting 1-(5-amino-2,4-dichlorophenyl)-4,5-dihydro-4-difluoromethyl-3-methyl-1,2,4-triazol-5(1H)-one with methanesulfonyl chloride at a reaction temperature between 5 to 15 degree centigrade in water under controlled pH conditions using sodium carbonate and a phase transfer catalyst suspended in an aromatic solution. The presence of the phase transfer catalyst in a 1:1 aromatic solution is necessary to ensure the rapid formation of the desired sulfonamide versus the competing hydrolysis of the highly reactive methanesulfonyl chloride.

Likewise the simultaneous addition of the methanesulfonyl chloride into the reaction while maintaining the pH reduces its hydrolysis rate allowing for significant formation of the desired sulfonamide as compared to the failed reactions shown in the prior art for example in X. Deng and N. S. Mati, *Green Chem.*, 2006, 8, 835-838. Thus the method uses only a slight excess of methanesulfonyl chloride and the resultant sulfonamide product is easily isolated in excellent yields and purity by simple filtration of the precipitated solid after acidification of the reaction. This method eliminates the use of organic solvents and amine scavenger bases and the procedure generates virtually no waste, which makes it an ideal green chemistry process.

DETAILED DESCRIPTION OF THE INVENTION

Before describing the present invention in detail, it is to be understood that the terminology used herein is for the purpose of describing particular embodiments only, and is not intended to be limiting.

In accordance with the present invention, there is provided a process to produce, in a highly environmentally benign and cost effective manner, the agrochemical herbicide N-[2,4-dichloro-5-[4-(difluoromethyl)-4,5-dihydro-3-methyl-5-oxo-1H-1,2,4-triazol-1-yl]phenyl]methanesulfonamide.

In one embodiment of the present invention, a process is described for the preparation of N-[2,4-dichloro-5-[4-(difluoromethyl)-4,5-dihydro-3-methyl-5-oxo-1H-1,2,4-triazol-1-yl]phenyl]methanesulfonamide by reacting 1.0 equivalent of 1-(5-amino-2,4-dichloro phenyl)-4,5-dihydro-4-difluoromethyl-3-methyl-1,2,4-triazol-5(1H)-one with 1.2 equivalent of methanesulfonyl chloride at 5 to 15 degree centigrade in water at 7.5 to 8.5 dynamic controlled pH condition achieved by using 1.1 to 1.4 equivalents of aqueous sodium carbonate solution together with 0.05 equivalent of a tetraalkylammonium halide phase transfer catalyst in 0.05 equivalent aromatic solvent for 30 minutes to 1 hour. Acidification of the reaction mixture led to direct precipitate of the desired product in excellent yield and purity.

It will be clear to those skilled in the art that modifications can be made to the process described herein without departing from the inventive concept set forth in our claims below.

Example 1

Preparation of N-[2,4-dichloro-5-[4-(difluoromethyl)-4,5-dihydro-3-methyl-5-oxo-1H-1,2,4-triazol-1-yl] phenyl]methanesulfonamide in water at 10 C with tetrabutylammonium bromide in toluene The solid 1-(5-amino-2,4-dichlorophenyl)-4,5-dihydro-4-difluoromethyl-3-methyl-1,2,4-triazol-5(1H)-one (1.0 equiv.) was suspended in 20 equivalent of water and the reaction mixture chilled to 10 C. Vigorous stirring was commenced and 0.05 equiv of tetrabutylammonium bromide in 0.05 equiv of toluene was added. Using a pH meter, the of the suspension was brought to 7.8 by adding adequate quantity of 1 molar sodium carbonate aqueous solution. Simultaneous addition of 1.2 equiv methanesulfonyl chloride was started into the reaction while keeping the flow of the aqueous sodium carbonate on such that the pH of 7.8 was maintained throughout. After 45 minutes the reaction was complete and the suspension was replaced by a clear solution. Concentrated hydrochloric acid was added slowly to bring the pH of the reaction to 2.0 wherein a precipitate was formed. The precipitate was collected by filtration, washed with water and dried to give the N-[2,4-dichloro-5-[4-(difluoromethyl)-4,5-dihydro-3-methyl-5-oxo-1H-1,2,4-triazol-1-yl] phenyl]methanesulfonamide as a white solid (0.96 equiv and 96% purity).

Example 2

Preparation of N-[2,4-dichloro-5-[4-(difluoromethyl)-4,5-dihydro-3-methyl-5-oxo-1H-1,2,4-triazol-1-yl] phenyl]methanesulfonamide in water at 10 C with tetrabutyl ammonium bromide but no aromatic solvent The solid 1-(5-amino-2,4-dichlorophenyl)-4,5-dihydro-4-difluoromethyl-3-methyl-1,2,4-triazol-5(1H)-one (1.0 equiv.) was suspended in 20 equivalent of water and the reaction mixture chilled to 10 C. Vigorous stirring was commenced and 0.05 equiv of tetrabutylammonium bromide was added. Using a pH meter, the pH of the suspension was brought to 7.8 by adding adequate quantity of 1 molar sodium carbonate aqueous solution. Simultaneous addition of 1.2 equiv methanesulfonyl chloride was started into the reaction while keeping the flow of the aqueous sodium carbonate on such that the pH of 7.8 was maintained throughout. After 30 minutes the reaction was not progressing as seen by TLC and the suspension was still present. Addition of 1.2 equiv more methanesulfonyl chloride and stirring for 1 hour did not change the TLC or suspended matter. Concentrated hydrochloric acid was added slowly to bring the pH of the reaction to 2.0 wherein the suspension dissolved and no new precipitate was formed nor any product isolated.

Example 3

Preparation of N-[2,4-dichloro-5-[4-(difluoromethyl)-4,5-dihydro-3-methyl-5-oxo-1H-1,2,4-triazol-1-yl] phenyl]methanesulfonamide in water at 10 C with tetrabutylammonium bromide in toluene without simultaneous addition of the methanesulfonyl chloride The solid 1-(5-amino-2,4-dichlorophenyl)-4,5-dihydro-4-difluoromethyl-3-methyl-1,2,4-triazol-5(1H)-one (1.0 equiv.) and 1.2 equiv of methanesulfonyl chloride was suspended in 20 equivalent of water and the reaction mixture chilled to 10 C. Vigorous stirring was commenced and 0.05 equiv of tetrabutylammonium bromide in 0.05 equiv of toluene was added. Using a pH meter, the pH of the suspension was brought to 7.8 by adding adequate quantity of 1 molar sodium carbonate aqueous solution and dynamically maintained for 1 hour. The suspension was much reduced but not eliminated. Concentrated hydrochloric acid was added slowly to bring the pH of the reaction to 2.0 Wherein a precipitate was formed. The precipitate was collected by filtration, washed with water and dried to give the N-[2,4-dichloro-5-[4-(difluoromethyl)-4,5-dihydro-3-methyl-5-oxo-1H-1,2,4-triazol-1-yl] phenyl]methanesulfonamide as a white solid (0.41 equiv and 91% purity).

Example 4

Preparation of N-[2,4-dichloro-5-[4-(difluoromethyl)-4,5-dihydro-3-methyl-5-oxo-1H-1,2,4-triazol-1-yl] phenyl]methanesulfonamide in water at 10 C with tetra-n-propyl ammonium chloride The solid 1-(5-amino-2,4-dichlorophenyl)-4,5-dihydro-4-difluoromethyl-3-methyl-1,2,4-triazol-5(1H)-one (1.0 equiv.) was suspended in 20 equivalent of water and the reaction mixture chilled to 10 C. Vigorous stirring was commenced and 0.05 equiv of tetra-n-propylammonium chloride in 0.05 equiv of xylene was added. Using a meter, the pH of the suspension was brought to 7.8 by adding adequate quantity of 1 molar sodium carbonate aqueous solution. Simultaneous addition of 1.2 equiv methanesulfonyl chloride was started into the reaction while keeping the flow of the aqueous sodium carbonate on such that the pH of 7.8 was maintained throughout. After 45 minutes the reaction was complete and the suspension was replaced by a clear solution. Concentrated hydrochloric acid was added slowly to bring the pH of the reaction to 2.0 wherein a precipitate was formed. The precipitate was collected by filtration, washed with water and dried to give the N-[2,4-dichloro-5-[4-(difluoromethyl)-4,5-dihydro-3-methyl-5-oxo-1H-1,2,4-triazol-1-yl] phenyl]methanesulfonamide as a white solid (0.92 equiv and 97% purity).

Example 5

Preparation of N-[2,4-dichloro-5-[4-(difluoromethyl)-4,5-dihydro-3-methyl-5-oxo-1H-1,2,4-triazol-1-yl] phenyl]methanesulfonamide in water at 10 C with potassium carbonate as the base The solid 1-(5-amino-2,4-dichlorophenyl)-4,5-dihydro-4-difluoromethyl-3-methyl-1,2,4-triazol-5(1H)-one (1.0 equiv.) was suspended in 20 equivalent of water and the reaction mixture chilled to 10 C. Vigorous stirring was commenced and 0.05 equiv of tetra-n-propylammonium chloride in 0.05 equiv of xylene was added. Using a pH meter, the of the suspension was brought to 7.8 by adding adequate quantity of 1 molar sodium carbonate aqueous solution. Simultaneous addition of 1.2 equiv methanesulfonyl chloride was started into the reaction while keeping the flow of the aqueous potassium carbonate on such that the of 7.8 was maintained throughout. After 45 minutes the reaction was complete and the suspension was replaced by a clear solution. Concentrated hydrochloric acid was added slowly to bring the pH of the reaction to 2.0 wherein a precipitate was formed. The precipitate was collected by filtration, washed with water and dried to give the N-[2,4-dichloro-5-[4-(difluoromethyl)-4,5-dihydro-3-methyl-5-oxo-1H-1,2,4-triazol-1-yl] phenyl]methanesulfonamide as a white solid (0.95 equiv and 97% purity).

Example 6

Preparation of N-[2,4-dichloro-5-[4-(difluoromethyl)-4,5-dihydro-3-methyl-5-oxo-1H-1,2,4-triazol-1-yl] phenyl]methanesulfonamide in water at 25 C with tetrabutylammonium bromide in toluene The solid 1-(5-amino-2,4-dichlorophenyl)-4,5-dihydro-4-difluoromethyl-3-methyl-1,2,4-triazol-5(1H)-one (1.0 equiv.) was suspended in 20 equivalent of water and the reaction mixture chilled to 25 C. Vigorous stirring was commenced and 0.05 equiv of tetrabutylammonium bromide was added. Using a pH meter, the pH of the suspension was brought to 7.8 by adding adequate quantity of 1 molar sodium carbonate aqueous solution. Simultaneous addition of 1.2 equiv methanesulfonyl chloride was started into the reaction while keeping the flow of the aqueous sodium carbonate on such that the pH of 7.8 was maintained throughout. After 15 minutes the reaction was not progressing as seen by TLC and the suspension was still present. Addition of 1.2 equiv more methanesulfonyl chloride and stirring for 1 hour more did not change the TLC or suspended matter. Concentrated hydrochloric acid was added slowly to bring the pH of the reaction to 2.0 wherein the suspension dissolved and no new precipitate was formed nor any product isolated.

What is claimed is:

1. A process to produce N-[2,4-dichloro-5-[4-(difluoromethyl)-4,5-dihydro-3-methyl-5-oxo-1H-1,2,4-triazol-1-yl] phenyl]methanesulfonamide consisting essentially of:
    (i) treating 1-(5-amino-2,4-di chlorophenyl)-4,5-dihydro-4-difluoromethyl-3-methyl-1,2,4-triazol-5(1H)-one and
    (ii) methane sulfonyl chloride in;
    (iii) water with an inorganic base under;
    (iv) controlled pH conditions and;
    (v) an alkylammonium halide phase transfer catalyst suspended in an aromatic solvent.

2. A process according to claim 1, wherein the reaction is carried out between 5 degree centigrade and 15 degree centigrade.

3. A process according to claim 1, wherein the pH in the reaction is dynamically maintained in the range between 7.5 and 8.5 using an aqueous inorganic base.

4. A process according to claim 3, wherein the inorganic base is sodium carbonate and potassium carbonate.

5. A process according to claim 1, wherein the methanesulfonyl chloride is added simultaneously with the aqueous inorganic base into the suspension of the 1-(5-amino-2,4-dichlorophenyl)-4,5-dihydro-4-difluoromethyl-3-methyl-1,2,4-triazol-5(1H)-one and alkylammonium halide phase transfer catalyst in an aromatic solvent.

6. A process according to claim 1 wherein the phase transfer catalyst and aromatic solvent are used in a 1:1 ratio.

7. A process according to claim 1 wherein the phase transfer catalyst used is tetrabutylammonium bromide or tetrapropylammonium chloride.

8. A process according to claim 1 wherein the aromatic solvent used is toluene or xylene.

* * * * *